United States Patent
Zimmermann et al.

(10) Patent No.: US 9,295,200 B2
(45) Date of Patent: Mar. 29, 2016

(54) TEMPERATURE-INDEPENDENT TURGOR PRESSURE MEASUREMENT DEVICE, METHOD FOR PRODUCING SAID MEASUREMENT DEVICE, AND A METHOD FOR TEMPERATURE COMPENSATION FOR SAID MEASUREMENT DEVICE

(75) Inventors: Ulrich Zimmermann, Falkensee (DE); Wilhelm Ehrenberger, Berlin (DE); Simon Rüger, Berlin (DE); Gertraud Zimmermann, Waldbrunn (DE)

(73) Assignee: YARA ZIM PLANT TECHNOLOGY GMBH, Hennigsdorf (DE)

( * ) Notice: Subject to any disclaimer, the term of this patent is extended or adjusted under 35 U.S.C. 154(b) by 408 days.

(21) Appl. No.: 13/983,752

(22) PCT Filed: Feb. 10, 2012

(86) PCT No.: PCT/EP2012/052295
§ 371 (c)(1),
(2), (4) Date: Aug. 5, 2013

(87) PCT Pub. No.: WO2012/107555
PCT Pub. Date: Aug. 16, 2012

(65) Prior Publication Data
US 2013/0305831 A1    Nov. 21, 2013

(30) Foreign Application Priority Data

Feb. 11, 2011 (DE) .......................... 10 2011 011 020
Jul. 27, 2011 (DE) .......................... 10 2011 079 905

(51) Int. Cl.
*G01L 19/04* (2006.01)
*A01G 7/00* (2006.01)
*B23P 19/00* (2006.01)
*G01N 33/00* (2006.01)
(Continued)

(52) U.S. Cl.
CPC . *A01G 7/00* (2013.01); *B23P 19/00* (2013.01); *G01L 9/045* (2013.01); *G01L 11/008* (2013.01); *G01L 19/147* (2013.01); *G01N 33/0098* (2013.01); *Y10T 29/49826* (2015.01)

(58) Field of Classification Search
CPC ........ G01D 19/04; G01D 9/065; G01D 9/125
USPC ..................................................... 73/708, 700
See application file for complete search history.

(56) References Cited

U.S. PATENT DOCUMENTS

| 6,277,637 B1 | 8/2001 | Lintilhac et al. |
| 2011/0049264 A1* | 3/2011 | Zimmermann .......... A01G 7/00 239/266 |

FOREIGN PATENT DOCUMENTS

| DE | 20218044 | 2/2003 |
| DE | 102006043058 | 3/2008 |

(Continued)

OTHER PUBLICATIONS

Written Opinion mailed Aug. 13, 2013 for PCT/EP2012/052295.
(Continued)

*Primary Examiner* — Lisa Caputo
*Assistant Examiner* — Jamel Williams
(74) *Attorney, Agent, or Firm* — Hauptman Ham, LLP

(57) ABSTRACT

The invention relates to a clamp element for a temperature-independent turgor pressure measurement device for measuring the turgor pressure in a plant sample.

64 Claims, 7 Drawing Sheets

(51) Int. Cl.
  *G01L 19/14* (2006.01)
  *G01L 9/04* (2006.01)
  *G01L 11/00* (2006.01)

(56) References Cited

FOREIGN PATENT DOCUMENTS

| DE | 102007057904 | 6/2009 | | |
|---|---|---|---|---|
| DE | 102009032872 | 1/2011 | | |
| WO | 2009092389 | 7/2009 | | |
| WO | WO 2011006620 A1 * | 1/2011 | ............... | A01G 7/00 |

OTHER PUBLICATIONS

International Search Report mailed Aug. 21, 2012 for PCT/EP2012/052295.

German Office Action issued Jan. 19, 2012 in the corresponding German priority application 10 2011 079 905.2.

Anja Geitmann, Experimental Approaches Used to Quantify Physical Parameters at Cellular and Subcellular Levels, Journal, 2006, 1380-1390, American Journal of Botany 93 (10), Montreal, Quebec, Canada.

Ruger Simon et al., Internet-Aktive Sonden Messen Die Wasserversorgung Von Pflanzen [Internet-Active Probes Measure the Water Supply of Plants], Online Article, http://www.laborpraxis.vogel.de/forschung-und-entwicklung/analytic/articles/254329/, May 18, 2010.

Zimmermann et al., Kontinuierliche Druckmessung in Pflanzenzellen [Continuous Pressure Measurement in Plant Cells], 1969, Naturwissenschaften 56, 634.

P.F. Scholander et al., Sap Pressure in Vascular Plants, retrieved on Feb. 9, 2011, Science, vol. 148.

M.T. Tyree et al., The Measurement of the Turgor Pressure and the Water Relations of Plants by the Pressure-Bomb Technique, Feb. 1972, Journal of Experimental Botany, No. 74, pp. 267-282, vol. 23.

Ulrich Zimmermann et al., Water Ascent in Tall Trees: Does Evolution of Land Plants Rely on a Highly Metastable State?, Tansley review, Germany.

* cited by examiner

TEMPERATURE-INDEPENDENT TURGOR PRESSURE MEASUREMENT DEVICE, METHOD FOR PRODUCING SAID MEASUREMENT DEVICE, AND A METHOD FOR TEMPERATURE COMPENSATION FOR SAID MEASUREMENT DEVICE

CROSS REFERENCE TO RELATED APPLICATION

This application claims the priority of European Patent Application No. 10 2011 011 020.8, filed on Feb. 11, 2011 and 10 2011 079 905.2 filed on Jul. 27, 2011 in the EPO (European Patent Office). Further, this application is the National Phase application of International Application No. PCT/EP2012/052295 filed Feb. 10, 2012, which designates the United States and was published in English.

The invention relates to a clamp element for a turgor pressure measurement device, a turgor pressure measurement device, a method for temperature compensation for a clamp element of a turgor pressure measurement device, a method for temperature compensation for a turgor pressure measurement device, a method for producing a clamp element for a turgor pressure measurement device and a method for operating a turgor pressure measurement device.

The invention makes use of the fact that the hydrostatic overpressure, i.e. the so-called turgor pressure, in plant cells is one of the most important plant parameters for detecting the state of a plant.

It is known that the turgor pressure provides information about the water supply of the plants. It is also known that the turgor pressure is caused by osmotic processes which in turn depend on the transport of substances. Thus, the turgor pressure also reflects the supply of the plants with nutrients. Finally, it is known that, depending on the plant species, the turgor pressure can be about 700 kPa (=7 bar) and that the turgor pressure drops to very low values of about 30 kPa to 50 kPa in case of a great dryness (water shortage) or high temperatures and/or a low relative air humidity. At a turgor pressure of zero, the plant cells die and thus also the plant. A sufficiently high turgor pressure is moreover important for the plant growth because the cell growth and many biophysical processes in the plant are controlled by the turgor pressure.

The practical meaning of the turgor pressure known in the field of agriculture is based on the fact that the quality of fruits often depends on the fact that plants are subjected to a slight water stress, leading to a sub-optimum turgor pressure. Known examples thereof are red grapevines or olives. The quality of the red wine and the quality of olives are improved considerably if the plants or trees are not sufficiently watered. Because of said importance of the turgor pressure in plants as a watering indicator, attempts have already been made for more than 60 years to detect the turgor pressure by measurement in order to achieve the optimum crop yield for the respective plant based on selective watering.

In view of the prior art, plasmolysis is known as a method for measuring the turgor pressure in plant-physiological laboratories, i.e. the leafs of the plant are cut off and transferred to solutions with increasing osmolarity. Based on the osmotic pressure occurring during plasmolysis (i.e. the separation of the cell membrane from the cell wall), the turgor pressure can be calculated. However, this method is disadvantageous in practical use because it is destructive, labor-intensive, very imprecise, cannot be automated and is not suitable for being used in fields in agriculture.

Progress in the determination of the turgor pressure has been made by developing the cell turgor pressure measurement probe. According to this method, a micro-capillary filled with incompressible oil is introduced under a microscope into a cell through the surrounding tissue, and the pressure is transferred via the oil phase to a pressure sensor (see Zimmermann et al., 1969, Kontinuierliche Druckmessung in Pflanzenzellen [continuous pressure measurement in plant cells], Naturwissenschaften 56, 634). This minimally invasive method is highly precise.

Various modifications of this probe type, which have been developed during the last 40 years but are all based on the development of the cell turgor pressure measurement probe, are already known (Zimmermann et al., 2004, Water ascent in tall trees: does evolution of land plants rely on a highly metastable state? New Phytologist, 575-615).

It is a disadvantage of the cell turgor pressure method that it is very difficult and complex. Moreover, it is not suitable for fields because it is very sensitive to wind. Therefore, long-term measurements in fields are not possible.

A further method for the indirect determination of relative changes in the turgor pressure (or the water potential), which is nowadays used under both laboratory and field conditions, is the pressure bomb method according to Scholander (Scholander et al., 1965, Sap Pressure in Vascular Plants. Science 148, 339-346; Tyree and Hammel, 1972, The Measurement of the Turgor Pressure and the Water Relations of Plants by the Pressure-bomb Technique. Journal of Experimental Botany 23, 267-282). According to this method, a leaf/plant organ is cut off and put under gas pressure in a pressure bomb. The pressure at which water exits at the cutting site that is in contact with the atmosphere is numerically equated with the water potential. However, said method is labor-intensive, destructive, very imprecise and, like the plasmolysis method, cannot be automated.

A non-invasive measurement for detecting relative changes in the turgor pressure was described in 1979 by Heathcote et al. and used in 1983 by Turner and Sobrado (in this connection, see also the overview by Geitmann, 2006, Experimental Approaches used to Quantify Physical Parameters at Cellular and Subcellular Levels. American Journal of Botany 93, 1380-1390). According to this method, a pressure is applied to the cell by means of a spring, and the deformation or the elasticity of the cell, which depends on the turgor pressure, is measured. Disadvantages are the inaccuracy of the method and the fact that it cannot be used for numerous plants in case the leafs of a plant are very rigid. Automation is not possible either, or it is possible with many efforts only.

The method by Heathcote et al. (1979) is known from the patent application DE 10 2006 043 058 A1 ("Zustandssensor für Pflanzen sowie Bewässerungsanlage mit einem derartigen Zustandssensor" [state sensor for plants and a watering system comprising a state sensor of this type]). However, applications of this method in practice have revealed that only in rare cases the turgor pressure corresponds to the values directly measured by using the cell turgor pressure measurement probe. The measurement curves mentioned in the application partly do not correspond to the real conditions, which explains why the Heathcote method has not established itself.

A patent application for a further method for turgor pressure measurement was filed by Lintilhac and Outwater on Mar. 23, 1999 in the United States of America (Method and Apparatus for Determining a Contact Area Between a Probe and a Specimen, U.S. Pat. No. 6,277,637 B1). This patent document is based on the idea that the shape of a cell and the contact between the cell and an instrument measuring the shape variation change as the turgor pressure changes. Therefore, this method can only be used for isolated cells but not for cells in a plant tissue.

Moreover, patent application WO 2009/092389 A1 is known. However, according to this suggested solution, a plurality of pressure pulses have to be applied after attaching the probe in order to obtain a homogeneous planar contact between plant sample and potting compound. In this connection, the leaf might basically be damaged and the measurement might become useless after a few hours or days.

Also patent application DE 10 2009 032 872 A1 is known, which relates to a method for producing a measurement device which is equipped to detect the state of a plant sample and which comprises a clamp means having a sensor clamp block and a counter clamp block for exerting a clamping pressure on the plant sample and a sensor device having a sensor for measuring a pressure response signal of the plant sample. According to this suggested solution, in practice there is the problem that the suggested production cannot be used for a mass production of probes. The required working steps are time-consuming and mostly cannot be automated. In particular the null measurement of the probe varies considerable after embedding the sensor into the polymeric and cross-linked matrix. There are voltage values between −15 mV and +15 mV, i.e. the sensor in the polymeric matrix is either under tensile load (in case of negative voltage values) or under an overpressure (in case of positive voltage values). Moreover, the zero value in the closed state is significantly different from the zero value in the open state (in case both magnets are folded apart), because in accordance with this suggestion the polymeric and cross-linked matrix is not introduced in a reproducible planar manner. Since the cells in a plant tissue (leaf, stem, etc.) are under an overpressure (the turgor pressure, 30 kPa to 700 kPa), a further, unknown zero shift can occur when introducing the leaf or another plant tissue between the sensor clamp block and the counter clamp block of the probe. In the above-mentioned example, hysteresis occurs when returning to the zero value of the sensor after application of relatively high pressure values (>50 kPa) because silicone and adhesive have different restoring properties, which act in a delayed manner on the sensor membrane. The greatest problem of the measurement devices produced in accordance with this method is mainly the temperature dependency of the probes after mounting and filling in of the polymer of more than 6 kPa per 10 degrees Celsius temperature change (change at the plant of about 5 to 100 kPa). A further ensuing disadvantage is the fact that the zero value changes as the temperature changes. Under field conditions, in particular in very dry and hot regions, the temperature can vary considerably (between 15 degrees Celsius during the night and 45 degrees Celsius during the day). Leafs in the shadow are exposed to a different temperature than leafs which are exposed to the direct solar irradiation. Thus, the zero shift caused by temperature fluctuations overlaps with fluctuations caused by changes in the turgor pressure so that an exact statement as regards the water content of the plant cannot be made. The temperature dependency of the zero value is mainly caused by an incomplete polymerization in the vicinity of the sensor, by a limited adhesion of the polymer to the wall of the probe housing, by incompletely polymerized micro-cavities and by inclusion of very little air bubbles. Although the temperature dependency of sensors can be compensated for by the span and offset method, experiments have shown that these methods are not successful in connection with the magnetic probes. Further, it is a disadvantage of the method described above that the bonding wires at the sensor can tear caused by different temperature expansions because a different material is used for fixing the bonding wires than for embedding the sensor in the polymer compound. These materials have different expansion coefficients. These probes are also disadvantageous because a homogeneous contact between probe and leaf can be achieved—if at all—only by a plurality of pressure pulses, as described in WO 2009/092389 A1. For the mass use in fields it is necessary that the measurement device can be attached and used by an unskilled farmer who does not have any special knowledge. As a result, only few probes (about 1% of the produced probes) that are produced in accordance with this patent application fulfill the requirements necessary for an exact measurement of the turgor pressure.

The known methods are moreover disadvantageous because either pressure pulses have to be applied (see WO 2009/092389 A1) or the temperature dependency of the probes is too strong (see WO 2009/092389 A1 and DE 10 2009 032 872 A1).

It is the object of the present invention to provide a clamp element for a turgor pressure measurement device, a turgor pressure measurement device, a method for temperature compensation for a clamp element of a turgor pressure measurement device, a method for temperature compensation for a turgor pressure measurement device, a method for producing a clamp element for a turgor pressure measurement device, a method for producing a turgor pressure measurement device and a method for operating a turgor pressure measurement device, which allow for the first time the production of a large number of probes which measure the turgor pressure without any falsification caused by temperature influences and which can be easily attached to a leaf by an unskilled person (e.g. farmer) without applying pressure pulses.

This object is achieved by the subject-matter and the methods of the independent claims. Advantageous embodiments and applications of the invention can be taken from the dependent claims.

According to the invention, the term "plant sample" means an intact plant, a plant organ or plant tissue or a separated part of a plant, a plant organ or plant tissue.

In view of the probe structure, one aspect of the invention starts out from the basic idea that a homogeneous top is achieved at the surface of the probe which comes in contact with the surface of the plant in one step (without the contact having to be achieved by the application of a plurality of pressure pulses). This should in particular be substantially independent of the temperature, i.e. the homogeneity of the top is preferably also guaranteed in case of temperature fluctuations. According to the invention, "homogeneous top" means, e.g., a surface which is suitable or adapted for achieving a uniform contact and/or the largest-possible contact area with the surface of the plant. For example, the surface of the probe corresponds to the surface of the plant in the meaning of the "key-lock" principle, at least substantially.

Furthermore, the invention starts out from the basic idea to embed the sensor of the probe in a polymer compound. According to the invention, a homogeneous embedding is achieved in that, on the one hand, a substantially complete, preferably complete adhesion is present between the polymer compound and the surrounding metal housing, on the other hand, substantially no gas bubbles (e.g., air bubbles) are present in the polymer compound, i.e. the polymer compound is substantially free of gas bubbles. For achieving the above-mentioned properties, the embedding must take place in several steps in accordance with the invention, i.e. in accordance with the invention the polymer compound must be introduced in several layers and must be arranged above the sensor in layers. Thus, the influence of temperature fluctuations is reduced considerably or eliminated.

According to a first aspect, the invention provides a method for producing a clamp element for a turgor pressure measurement device for measuring the turgor pressure in a plant sample. The clamp element produced in accordance with the invention has a sensor receiving portion with a first contact surface, a surface lying opposite the contact surface, and a peripheral surface connecting the two, wherein the clamp element has a longitudinal axis extending perpendicularly to the first contact surface, and with a recess which is on the side of, and opening towards, said first contact surface. The clamp element further comprises a pressure sensor, which is arranged on a printed circuit board/lead frame, to measure a pressure response signal of the plant sample, said printed circuit board/lead frame being arranged with the pressure sensor in the recess of the sensor receiving portion such that the pressure sensor faces the first contact surface and the printed circuit board/lead frame lies at the bottom of the recess. The clamp element of the present invention is preferably produced in accordance with the following steps:

(a) Fixing the printed circuit board/lead frame with the pressure sensor arranged thereon at the bottom of the recess or at the wall of the recess;

(b) filling a first amount of potting or casting material into the recess, wherein the first amount is selected such that only the printed circuit board/lead frame and the pressure sensor are covered and the potting compound can raise at the lower half of the inner wall of the sensor housing;

(c) after cross-linking the first amount of potting material with the printed circuit board/lead frame, the pressure sensor and the inner wall, filling in a second amount of potting material so that, taking into account the expansion during cross-linking of the second amount of potting material with the wall of the recess, the second amount of potting material remains below the upper edge of the recess; and (d) after cross-linking of the second amount of potting material with the recess wall, filling in a third amount of potting material so that the top of the potting material lies flush with the first contact surface.

According to a further aspect, the invention provides a clamp element for a turgor pressure measurement device for measuring the turgor pressure in a plant sample, said clamp element being produced in accordance with said method according to the invention.

Before the third amount of potting material has cured completely, a negative top structure is preferably formed on the surface of the potting material in accordance with a surface structure of a plant.

The negative top structure is preferably stamped into the surface of the potting material. Particularly preferably, the top structure is made by means of a counter clamp element of the turgor pressure measurement device having a corresponding counter structure.

In accordance with an alternative embodiment, a negative top structure is formed on the surface of the potting material in accordance with a surface structure of a plant, after the third amount of potting material has cured completely. Such structure can be made by means of the counter clamp element of the turgor pressure measurement device having a corresponding counter structure. For example, this is realized by stamping with the counter clamp element of the turgor pressure measurement device at a temperature of about 30° C. for a time period of 24 to 120 hours.

A transfer material can be clamped between the third amount of potting material of the clamp element and the counter clamp element.

The negative top structure is preferably substantially concave.

Thus, according to the invention, the polymer is introduced into the housing in three steps: during the first step, the polymer is introduced in such an amount that the printed circuit board/lead frame with the pressure sensor can be embedded without cavities and a homogeneous contact with the inner wall of the sensor receiving portion is obtained. After cross-linking with the printed circuit board/lead frame, the pressure sensor and the housing wall and after complete curing of the polymer, polymer is introduced in such an amount that, taking into account the expansion during cross-linking, the upper edge of the housing is not reached. In the third step, after cross-linking, the amount (normally in the nanoliter range) of polymer injected into the housing is such that preferably a planar, accurately fitting top of the housing is achieved.

Instead of silicone or polymers, silicones or polymers containing dies for detecting oxygen released by the leaf of the plant that is measured can be used for the filling.

Preferably, in a further step, the homogeneous top of the polymer compound is made, wherein said top is not planar but based on shapes corresponding to the plant surfaces (e.g. bent surfaces such as those present in a stem or in leafs having many veins).

According to the invention, structures are introduced into the surface of the magnetic counter stamp, e.g., by milling (e.g. concentric rings). In case of a possible overpressure in the cross-linked polymer, the relatively elastic polymer compound can expand via the structured depressions in the counter stamp, so that the overpressure is reduced and a stable zero is adjusted; said zero does not shift in case of a temperature change because of the structured expansion surfaces in the counter stamp, and at the same time a homogeneous contact between the two magnets and a leaf clamped between them is achieved due to said zero.

According to a preferred embodiment, the probe according to the invention is exposed to rapid temperature changes of maximally 110° C. and minimally −10° C. during and after polymerization in order to release possible stress in the material and structural inhomogeneities in the polymer. The period of these temperature changes is, e.g., 10 minutes. During this process, the probe is connected to a measurement device, e.g., a volt meter, and the process is carried out until a stable value in the form of a constant voltage is reached.

According to an alternative aspect, the invention provides a clamp element for a turgor pressure measurement device for measuring the turgor pressure in a plant sample, wherein the clamp element comprises a sensor receiving portion, a first force element and a pressure sensor arranged on a printed circuit board/lead frame. The sensor receiving portion has a first contact surface, a surface lying opposite the contact surface, and a peripheral surface connecting the two. The clamp element has a longitudinal axis extending perpendicularly to the first contact surface. Moreover, the clamp element has a recess on the side of the first contact surface, wherein the recess is open towards the first contact surface and wherein the sensor receiving portion has a through channel extending from the interior of the recess to an outer surface. The first force element is arranged on the surface of the sensor receiving portion which lies opposite the first contact surface. The pressure sensor, which is arranged on a printed circuit board/lead frame, is adapted for measuring a pressure response signal of the plant sample. The printed circuit board/lead frame is arranged with the pressure sensor in the recess of the sensor receiving portion in such a manner that the pressure sensor faces the first contact surface and the printed circuit board/lead frame lies at the bottom of the recess. Moreover, the printed circuit board/lead frame comprises a through channel extending from the side of the printed circuit board/ lead frame facing the recess opening to the side facing the bottom of the recess, wherein the opening of the through channel on the side facing the bottom is flush with the inner opening of the through channel of the sensor receiving portion. The recess is filled with a cured potting material with homogeneous top at the first contact surface.

According to a preferred embodiment, the printed circuit board/lead frame comprises at least two through channels extending from the side of the printed circuit board/lead frame facing the recess opening to the side of the printed circuit board/lead frame facing the bottom of the recess.

Moreover, it is preferred that the sensor receiving portion comprises at least two through channels extending from the interior of the recess to an outer surface, wherein the through channel openings on the side of the printed circuit board/lead frame facing the recess bottom are flush with inner openings of the through channels of the sensor receiving portion.

The holes serve for introducing, e.g., a potting polymer and for the escape of the polymer, so as to allow a completely planar filling with polymer and matrix cross-linking substances, as already discussed above.

Preferably, the printed circuit board/lead frame supporting the pressure sensor has a thermal expansion coefficient in the x and y directions of less than $12 \times 10^{-6}$ K$^{-1}$, in particular less than $16 \times 10^{-6}$ K$^{-1}$. In the z direction, the printed circuit board/lead frame preferably has a thermal expansion coefficient of less than $40 \times 10^{-6}$ K$^{-1}$, in particular less than $60 \times 10^{-6}$ K$^{-1}$. The printed circuit board/lead frame has a small expansion coefficient in the z direction because the expansion in the z direction would influence the surface of the sensor and thus the contact with the plant in a temperature-dependent manner.

The pressure sensor is preferably glued to the printed circuit board/lead frame. According to the invention, a maximum of 10 nl of adhesive (e.g., ACC Silicone AS5720) should be used for fixing the sensor to the printed circuit board/lead frame, said adhesive having an expansion coefficient which is comparable to or smaller than that of the embedding polymer.

The cross-section of the printed circuit board/lead frame preferably corresponds to the cross-section of the recess. Thus, it can be introduced into the surrounding housing in an accurately fitting manner. It is then no longer necessary to center the sensor under the microscope.

Preferably, the sensor receiving portion has an adhesive layer between the bottom or the wall of the recess and the side of the printed circuit board/lead frame facing the bottom/wall. The material of the adhesive has an expansion coefficient which is similar to that of the potting material.

The potting material is preferably not transparent to ultraviolet radiation. According to a further preferred embodiment, the potting material comprises a dye which is not transparent to ultraviolet radiation. This serves the purpose of eliminating or at least reducing the light dependency of the silicon chip of the sensor, so that the measured pressure signal is not falsified by incident light. Before being mixed with the potting material, the dye can be degassed for one day at a negative pressure of at least 700 kPa. The polymer degassed in this manner is then filled under a vacuum or at a negative pressure of at least 700 kPa into the housing of the sensor clamp element comprising the printed circuit board/lead frame.

The walls of the recess of the sensor receiving portion preferable do not contain an adhesion promoter, i.e. are free of an adhesion promoter.

According to an alternative aspect of the invention, a clamp element for a turgor pressure measurement device for measuring the turgor pressure in a plant sample is provided, said clamp element comprising: a sensor receiving portion with a first contact surface, a surface lying opposite the contact surface, and a peripheral surface connecting the two, wherein the clamp element has a longitudinal axis extending perpendicularly to the first contact surface, and with a recess which is on the side of, and opening towards, said first contact surface, a pressure sensor, which is arranged on a printed circuit board/lead frame, to measure a pressure response signal of the plant sample, said printed circuit board/lead frame being arranged with the pressure sensor in the recess of the sensor-receiving portion such that the pressure sensor faces the first contact surface and the printed circuit board/lead frame lies at the bottom of the recess, and wherein the recess is filled with a cured potting material which is not transparent to ultraviolet radiation. The potting material preferably comprises a dye which is not transparent to ultraviolet radiation. As already explained, this serves for eliminating or at least reducing the light dependency of the silicon chip of the sensor, so that the measured pressure signal is not falsified by incident light. Before being mixed with the potting material, the dye can be degassed for one day at a negative pressure, as described.

According to a further aspect, the invention provides a clamp element for a turgor pressure measurement device for measuring the turgor pressure in a plant sample. The clamp element comprises a sensor receiving portion with a first contact surface, a surface lying opposite the contact surface, and a peripheral surface connecting the two. The clamp element has a longitudinal axis extending perpendicularly to the first contact surface, as well as a recess on the side of the first contact surface, wherein said recess is open towards the first contact surface. The clamp element further comprises a first force element which is arranged on the surface of the sensor receiving portion which is opposite the first contact surface. Moreover, a pressure sensor, which is arranged on a printed circuit board or lead frame, is provided for measuring a pressure response signal of the plant sample, wherein said printed circuit board/lead frame is arranged with the pressure sensor in the recess of the sensor-receiving portion such that the pressure sensor faces the first contact surface and the printed circuit board/lead frame lies at the bottom of the recess. The recess is filled with a cured potting material with homogeneous top at the first contact surface. Furthermore, the clamp element or the measurement signal of the clamp element is temperature-compensated as a whole.

The clamp element or its measurement signal is preferably temperature-compensated as a whole by linear regression. This is in contrast to known span and offset methods, which are not successful in the measurement devices of the present invention. In a preferred embodiment, the temperature compensation by linear regression can be carried out by the hardware. In accordance with a further embodiment, the temperature compensation can also be carried out by the software. The temperature compensation will be explained in detail in the following.

According to a further aspect, the invention provides a turgor pressure measurement device for measuring the turgor pressure in a plant sample. Said device comprises a first clamp element and a second clamp element. The first clamp element is a clamp element according to the first aspect of the invention. The first clamp element comprises a sensor receiving portion with a first contact surface, a surface lying opposite the contact surface, and a peripheral surface connecting the two. The clamp element has a longitudinal axis extending perpendicularly to the first contact surface, as well as a recess on the side of the first contact surface, wherein the recess is open towards the first contact surface. The clamp element moreover comprises a first force element which is arranged on the surface of the sensor receiving portion which is opposite the first contact surface. Moreover, a pressure sensor, which is arranged on a printed circuit board/lead frame, is provided for measuring a pressure response signal of the plant sample, the printed circuit board/lead frame with the pressure sensor being arranged in the recess of the sensor receiving portion such that the pressure sensor faces the first contact surface and the printed circuit board/lead frame lies at the bottom of the recess. The recess is filled with a cured potting material with homogeneous top at the first contact surface. The second clamp element has a counter clamp part with a second contact surface, a surface lying opposite the contact surface, and a peripheral surface connecting the two, as well as a second force element which is arranged on the side opposite the second contact surface. One of the two force elements has a magnet. Moreover, the turgor pressure measurement device or its measurement signal is temperature-compensated as a whole.

The temperature compensation solution according to the invention is advantageous because it is applied to the probe or the measurement device as a whole. In the prior art, solely the sensor chip is compensated for.

Also the temperature compensation for the turgor-pressure measurement device or its measurement signal as a whole is preferably carried out by linear regression. To this end, for example, in a first step a regression line for the temperature dependency of the output signal of the measurement device can be determined, and subsequently a compensated pressure signal can be calculated. For example, this is done in accordance with the equation $V[p]=V[p, T]-((T \cdot m)+t)$, wherein $V[p, T]$ is the output signal which depends on the pressure and temperature, T is the temperature, m is the gradient of the regression line and t is the y-axis section of the regression line.

As an alternative to this software-based temperature compensation, the compensation can be carried out in a hardware-based manner. To this end, again the regression line for the temperature dependency of the output signal of the measurement device can be determined, in order to then connect an electrical component, such as a resistor or a diode, in series with the output signal of the pressure sensor chip of the measurement device, wherein the electrical component has a temperature dependency being contrary to the regression line.

The turgor pressure measurement device or probe according to the present invention thus consists of a sensor clamp block and a counter clamp block. The sensor, preferably a pressure sensor, is embedded in the sensor clamp block. The two clamp blocks are preferably made of a metallic material.

Both in the clamp element and in the turgor pressure measurement device, the sensor receiving portion can have a through channel which extends from the interior of the recess to an outer surface, and the printed circuit board/lead frame can have a through channel which extends from the side of the printed circuit board/lead frame facing the recess opening to the side facing the bottom of the recess. The opening of the through channel on the side facing the bottom is flush with the inner opening of the through channel of the sensor receiving portion. Thus, the air can be allowed to escape during filling in or casting of the polymer compound, so that no air inclusions are formed.

According to a preferred embodiment, the printed circuit board/lead frame comprises at least two through channels extending from the side of the printed circuit board/lead frame facing the recess opening to the side of the printed circuit board/lead frame facing the bottom of the recess.

Moreover, it is preferred that the sensor receiving portion comprises at least two through channels which extend from the interior of the recess to an outer surface, wherein the through channel openings on the side of the printed circuit board/lead frame facing the recess bottom are flush with inner openings of the through channels of the sensor receiving portion.

The holes serve for introducing, e.g., the potting polymer (e.g. silicone; SYLGARD® 186 SILICONE ELASTOMER KIT) and for the escape of the polymer, so that a complete, planar filling with polymer and matrix cross-linking substances is possible. The potting material comprises, e.g., a cross-linkable polymer or consists of a cross-linkable polymer. For example, the potting material is selected from epoxy resin, silicone, additively cross-linking silicone, silicone cross-linking in a condensing manner, organic hydrogel or natural hydrogel having a thermal conductivity of $>0.4$ Watt$\times m^{-1} \times K^{-1}$. According to the invention, preferably polymers (which form concave meniscuses) are used, which, due to their surface tension properties, raise at the inner walls of the sensor clamping block when being introduced into the housing and thus realize a homogeneous contact therewith. Moreover, depending on the potting compound used, the optimum temperature at which the surface tension effects have the above-mentioned properties has to be taken into consideration. Therefore, the polymerization must be carried out in a narrow temperature interval (e.g., between about 20° C. and about 23° C.).

The printed circuit board/lead frame supporting the pressure sensor preferably has a thermal expansion coefficient in the x and y directions of less than $12 \times 10^{-6}$ K$^{-1}$, in particular less than $16 \times 10^{-6}$ K$^{-1}$. In the z direction, the printed circuit board/lead frame preferably has a thermal expansion coefficient of less than $40 \times 10^{-6}$ K$^{-1}$, in particular less than $60 \times 10^{-6}$ K$^{-1}$. The printed circuit board/lead frame has a small expansion coefficient in the z direction because the expansion in the z direction would influence the surface of the sensor and thus the contact with the plant in a temperature-dependent manner.

The pressure sensor is preferably glued to the printed circuit board/lead frame. According to the invention, a maximum of 10 nl of adhesive (e.g., ACC Silicone AS5720) should be used for fixing the sensor to the printed circuit board/lead frame, said adhesive having an expansion coefficient which is comparable to or smaller than that of the embedding polymer.

The cross-section of the printed circuit board/lead frame preferably corresponds to the cross-section of the recess. Thus, it is possible to introduce the printed circuit board/lead frame into the surrounding housing in an accurately fitting manner. It is then no longer necessary to center the sensor under the microscope.

Preferably, the sensor receiving portion has an adhesive layer between the bottom or the wall of the recess and the side of the printed circuit board/lead frame facing the bottom/wall. The material of the adhesive has an expansion coefficient which is similar to that of the potting material.

The potting material is preferably not transparent to ultraviolet radiation. According to a further preferred embodiment, the potting material comprises a dye which is not transparent to ultraviolet radiation. This serves the purpose of eliminating or at least reducing the light dependency of the silicon chip of the sensor, so that the measured pressure signal is not falsified by incident light. Before being mixed with the potting material, the dye can be degassed for one day at a negative pressure of at least 700 kPa. The polymer degassed in this manner is then filled under a vacuum or at a negative pressure of at least 700 kPa into the housing of the sensor clamp element comprising the printed circuit board/lead frame.

If the walls of the housing are not coated with the polymer caused by the surface tension effects, in accordance with a preferred embodiment, the walls of the housing are coated (e.g. by centrifugation) with a light, stable film of the polymer before introduction of the polymer, so that no cavities are formed between the polymer and the inner walls of the sensor clamp block during cross-linking of the polymer. The embedding polymer is preferably filled in in a plurality of steps in order to obtain a homogeneous contact between inner wall and polymer. During the first filling step, care should be taken that the still liquid polymer raises homogeneously at the wall of the container caused by surface tension effects, so that a homogeneous adhesion between polymer and wall is obtained.

In the turgor pressure measurement device, the second contact surface of the second clamp element is preferably structured. The structure can be present in the form of a relief. The structure can, e.g., be present in the form of concentric rings. This helps to increase the contact with the plant sample, because the rings impart a certain elasticity to the surface. Furthermore, it is preferred that the structure is present in the form of parallel grooves, wherein the groove being closest to the longitudinal axis is deeper than the remaining grooves. In case of a possible overpressure in the cross-linked polymer, the relatively elastic polymer compound can then expand via the structured depressions in the counter stamp, so that the overpressure is reduced and a stable zero is adjusted; said zero does not shift in case of a temperature change because of the structured expansion surfaces in the counter stamp, and due to said zero a homogeneous contact between the two magnets and a leaf clamped between them is at the same time achieved. Parallel grooves are suitable for the measurement of needles or for leafs, wherein the central, deeper groove can receive the central vein of the leaf. In general, a uniform and greatest-possible contact is provided.

According to a further aspect, the invention provides a method for the temperature compensation for a clamp device of a turgor pressure measurement device for measuring the turgor pressure in a plant sample, wherein according to the invention, the clamp device or its measurement signal is temperature-compensated as a whole by linear regression.

According to a further aspect, the invention provides a method for the temperature compensation for a turgor pressure measurement device for measuring the turgor pressure in a plant sample, preferably a turgor pressure measurement device according to the second aspect of the invention, wherein the measurement device or its measurement signal is temperature-compensated as a whole by linear regression.

Preferably, the temperature compensation is carried out in a software-based manner and comprises the steps of
(a) determining a regression line for the temperature dependency of the output signal of the measurement device; and
(b) calculating a compensated pressure signal in accordance with the equation $$V[p]=V[p,T]-((T\cdot m)+t),$$

wherein:
V[p, T] is the output signal which depends on pressure and temperature,
T is the temperature;
m is the gradient of the regression line; and
t is the y-axis section of the regression line.
Thus, on the basis of the regression line, first the gradient (m) and the y-axis section (t) are determined. For compensating for the temperature dependency, V[p] (compensated output signal) is calculated in accordance with the equation $V[p]=V[p, T]-((T\cdot m)+t)$. Since, in accordance with the above equation, the probe signal also depends on the pressure, the pressure dependency of the probe is subsequently determined by calibrating the probe in accordance with the air pressure. By using suitable software, the temperature-compensated signal V[p] is stored in the database and preferably visualized accordingly.

Step (a) preferably comprises the steps:
(a1) applying a gradual temperature increase to the measurement device in stages of 10° C. from 0° C. to 50° C. in intervals of at least 30 min each;
(a2) measuring the output signal of the measurement device at the respective stage; and
(a3) determining the regression line based on the measurement values.

In accordance with this software solution, the linear relation between temperature and output signal is used. The temperature is increased every 30 minutes by 10 degrees Celsius from 0 to 50 degrees Celsius, and at the same time the output signals of the probes are recorded.

Moreover, the probe is preferably calibrated in accordance with the air pressure and the temperature-compensated signal V[p] is stored for each measurement device in a database.

In accordance with this temperature compensation, preferably a "preconditioning" takes place. First, cooling to 0° C. takes place until stable values are reached (at least 10 minutes no value fluctuations within the measurement accuracy and the natural noise) of both the uncompensated output signal and the temperature measurement. In this connection, potting compounds having high thermal conductivities are preferred because they accelerate the adjustment of the equilibrium between sensor and environment.

The temperature measurement for the compensation can be carried out in many ways. For one, the temperature can be measured by means of a diode in the sensor housing (e.g., on printed circuit board/lead frame) or via the overall bridge resistance of the Wheatstone bridge (terminals of the supply voltage V+ and GND). This overall bridge resistance is temperature-dependent but not pressure-dependent. Alternatively, a pressure sensor chip with integrated temperature diode can be used.

For example, uncompensated measurement values are determined first. Then, the measurement device is switched to the pressure measurement mode in order to carry out a pressure measurement. Then, it is switched again to the temperature mode for temperature measurement. Now the pressure value is compensated for. For example, 1 to 2 ms lie between pressure measurement and temperature measurement.

Alternatively, the temperature is compensated for by using hardware. This can be done in two different ways. In this connection it is taken into consideration that the printed circuit board/lead frame comprises a measuring bridge, for example a Wheatstone bridge, in addition to the pressure sensor.

According to an alternative, the temperature dependency is compensated for by adequate replacement circuits (e.g. by resistors, diodes, etc. which are connected in parallel or in series) if the members of the Wheatstone bridge are closed (but also in the open state). To this end, first a regression line is determined for the temperature dependency of the output signal of the measurement device. Then, for example, an electrical component is connected in series with the output signal of the pressure sensor chip of the measurement device, wherein the electrical component has a temperature dependency that is contrary to the regression line.

Alternatively, also the individual elements of the measuring bridge can be changed if they are open, i.e. if the Wheatstone bridge is not closed and the individual resistors are accessible. In any case, the compensation device must lie in the close vicinity in order to avoid different temperatures of the probe and the compensation resistor. The output signal is then compensated for permanently. A temperature measurement is superfluous because the "correction resistance" changes as the temperature changes.

For example, at least one element or all pressure-dependent elements of the Wheatstone bridge of the pressure sensor are open, so that they can be changed by laser removal or other methods such that the temperature dependency is compensated for in a large range.

When using the probe according to the invention, occurring temperature fluctuations are preferably compensated for in that the pressure sensor is used in a double function also for the temperature measurement. For this purpose, the sensor is continuously switched between pressure measurement and temperature measurement, for example in a rhythm of 1 to 2 ms.

A further aspect of the invention relates to a method for operating a turgor pressure measurement device for measuring the turgor pressure in a plant sample, comprising
(a) a first clamp element which comprises:
  a sensor receiving portion with a first contact surface, a surface lying opposite the contact surface, and a peripheral surface connecting the two, wherein the clamp element has a longitudinal axis extending perpendicularly to the first contact surface, and with a recess on the side of the first contact surface, wherein the recess is open towards the first contact surface;
  a first force element which is arranged on the surface of the sensor receiving portion which is opposite the first contact surface;
  a pressure sensor, which is arranged on a printed circuit board/lead frame, to measure a pressure response signal of the plant sample, the printed circuit board/lead frame being arranged with the pressure sensor in the recess of the sensor receiving portion such that the pressure sensor faces the first contact surface and the printed circuit board/lead frame lies at the bottom of the recess;
  wherein the recess is filled with a cured potting material with a homogeneous top at the first contact surface;
(b) a second clamp element which comprises:
  a counter clamp part with a second contact surface, a surface lying opposite the second contact surface, and a peripheral surface connecting the two;
  a second force element which is arranged on the surface opposite the second contact surface;
wherein the method comprises the steps:
alternately measuring a pressure response signal of the plant sample in a pressure measurement mode of the measurement device and measuring the temperature of the surface of the plant sample in a temperature mode of the measurement device.

Thus, the temperature is detected directly at the surface of the leaf or the plant tissue by means of the probe, so that the temperature dependency of the probe can be compensated for by means of a corresponding hardware and/or software. The pressure signal can thus be compensated for in view of the temperature dependency.

For this purpose, the pressure measurement sensor is operated alternately in a pressure measurement mode and in a temperature measurement mode. According to a preferred embodiment, it is continuously shifted between the pressure measurement mode and the temperature measurement mode. For example, this is done in intervals of 1 to 2 ms.

Thus, the invention allows a lot of new applications.

For example, a further aspect of the invention relates to a method for operating a system consisting of a plurality of turgor pressure measurement devices for measuring the turgor pressure of a plant sample. The plurality of turgor pressure measurement devices are attached at the same plant sample and have distance sensors for determining the distances between the measurement devices. The method comprises the steps: detecting the distances between the measurement devices in pairs with respect to each other at two subsequent time points, and comparing the detected distance values for each individual pair of measurement devices to determine the plant growth.

Thus, a plurality of probes can be coupled electrically with each other so that when attaching the probes at different places of the plant (e.g., along the stem), the pressure transmission and/or the flow rate or air embolisms (cavities) between the probe sites can be measured. In addition, a distance sensor is introduced into the sensors, which thus provide the distances between the sensors in a telemetric manner. Quantification of the plant growth is moreover possible on the basis of the distance measurements.

By using RFID chips, the data of the probes can moreover be transmitted in a wireless manner.

Another method according to the invention for operating a system consisting of a plurality of turgor pressure measurement devices for measuring the turgor pressure in a plant sample, which are attached to the same plant sample, and wherein the measurement device and/or a separate device comprises an electromagnet that can be activated, comprises the steps:
  applying a pressure pulse to the plant sample by means of the electromagnet;
  detecting the pressure pulse propagating in the plant sample at the measurement devices;
  determining the propagating speed of the pressure pulse based on the time distance between pressure pulse generation and detection at the measurement devices for each measurement device and on the local distance between the measurement device/device generating the pressure pulse and the detecting measurement device; and
  determining the proportion of water-filled and air-filled spaces in the tissue of the plant sample based on the propagation speed of the pressure pulse.

In a preferred embodiment, the use of electromagnets allows transient pressure pulses to be applied locally to the leaf, so that the transmission and propagation speeds of the pressure in the leaf can be measured. Based thereon, information about the proportion of water-filled and air-filled spaces in the plant tissue can be obtained.

A further aspect of the invention relates to a system for plant watering, comprising a plurality of turgor pressure measurement devices for measuring the turgor pressure in a plant sample and a measurement device for detecting the activity of social pollinators, wherein in case an activity of the social pollinators is detected and at the same time a water shortage in the plant is detected, watering is activated.

Thus, the probe technique of the invention can be coupled with a measurement device for the pollination flight of social pollinators (bees, bumblebees, etc.) or other pollinating animals, i.e. with a measurement device measuring the activity of the pollinators.

The measurement devices of the invention can also be used in combination with devices for measuring the soil moisture, dendrometers, sap flow sensors, photosynthesis sensors, chlorophyll sensors, light sensors, wind sensors, temperature sensors and moisture sensors as well as with probes measuring the water amount per time unit in watering hoses (flow meters for water and for water plus fertilizers, additives, etc.).

In the following, the invention will be explained in more detail with reference to the drawings in which FIG. 1 shows a schematic sectional view of the measurement device of the invention according to a preferred embodiment;

Figure 1:
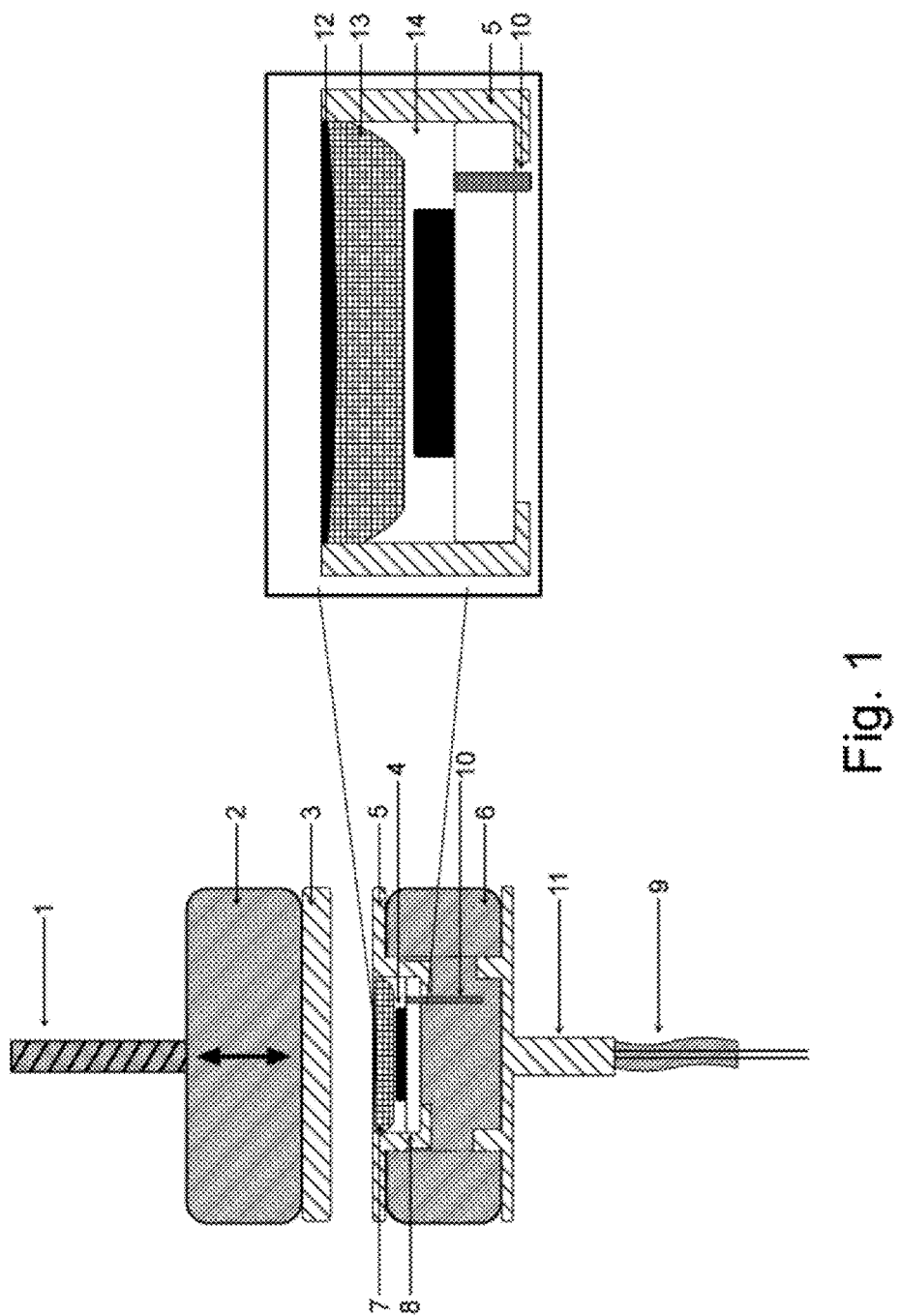
FIG. 1 shows a preferred embodiment of the measurement device of the invention.

The measurement device of the invention comprises a clamp element in the form of a magnet 6. The clamp element 6 in turn comprises a depression in which a sensor holder 5 is arranged, said sensor holder 5 forming the top of the clamp element facing the plant sample. A sensor insert is received in the depression of the sensor holder. The sensor insert comprises a printed circuit board or lead frame 8 which holds a pressure sensor 4. The pressure sensor 4 is connected with an evaluation device via activation lines 9 or via a wireless connection.

As shown in the enlarged view, the pressure sensor of the clamp element of the invention is cast or embedded in the depression of the sensor holder. According to the invention, this is preferably done in three steps or stages, which are shown by the three layers 14, 13 and 12. Polymer layer 14 is the layer which is filled in first and raises at the wall of the sensor insert. The second polymer layer 13 is applied on top thereof, before then the final layer 12 is cast.

A through channel 10 is provided for ventilation during casting. Said through channel extends through the printed circuit board and the magnet 6 to allow the air present in the recess to escape while the potting material is filled in.

An end housing 11 is preferably provided at the lower end, i.e. on the side facing away from the plant sample.

FIG. 1 moreover shows the counter clamp element comprising a counter stamp 3, a magnet 2 and a rod with screw thread 1.

The clamp element and the counter clamp element are aligned so as to be opposite one another and thus can be placed on opposite surfaces of a plant sample. The two elements are arranged perpendicularly with respect to the surface of the plant sample.

By means of the screw thread 1, the position of the magnet 2 of the counter clamp element can be adjusted relative to the counter stamp 3. Depending on the axial position of the magnet 2 at the rod 1, the force applied by the counter clamp element to the clamp element is higher or lower. To this end, the magnet has, e.g., a central opening with an internal thread. It is thus possible to adjust the distance between the magnet 2 and the magnet 6. Since the magnetic interaction between the magnets depends on their distance from each other, rotating the magnet 2 thus leads to a selective adjustment of the clamping pressure of the clamp device.

In the shown embodiment, the contact surface of the sensor holder of the clamp element has the same shape and size as the counter stamp 3 of the counter clamp element. No matter how the dimensions might be, care should be taken that covering of the active sensor surface is guaranteed.

As shown in FIG. 1, the surface of the clamp element and also the surface of the counter stamp 3 are planar. As exemplarily shown in FIG. 2, also other surfaces are conceivable, for example for the measurement of other plant parts, e.g. a stem or a needle.

When producing the clamp element, the printed circuit board/lead frame with the pressure sensor arranged thereon is preferably first glued to the bottom of the recess of the magnet 6. Then, a first amount of potting material 14 is filled into the recess, wherein the first amount is selected such that only the printed circuit board/lead frame and the pressure sensor are covered and the potting compound can raise at the lower half of the inner wall of the sensor housing. After the first amount of potting material has cross-linked with the printed circuit board/lead frame, the pressure sensor and the inner wall and has cured, a second amount of potting material 13 is filled in so that, taking into account the expansion during cross-linking of the second amount of potting material with the wall of the recess, the second amount of potting material remains below the upper edge of the recess. Finally, after the second amount of potting material has cross-linked with the recess wall, a third amount of potting material 12 is filled in so that the top of the potting material 12 lies flush with the first contact surface of the sensor holder 5.

Figure 2:
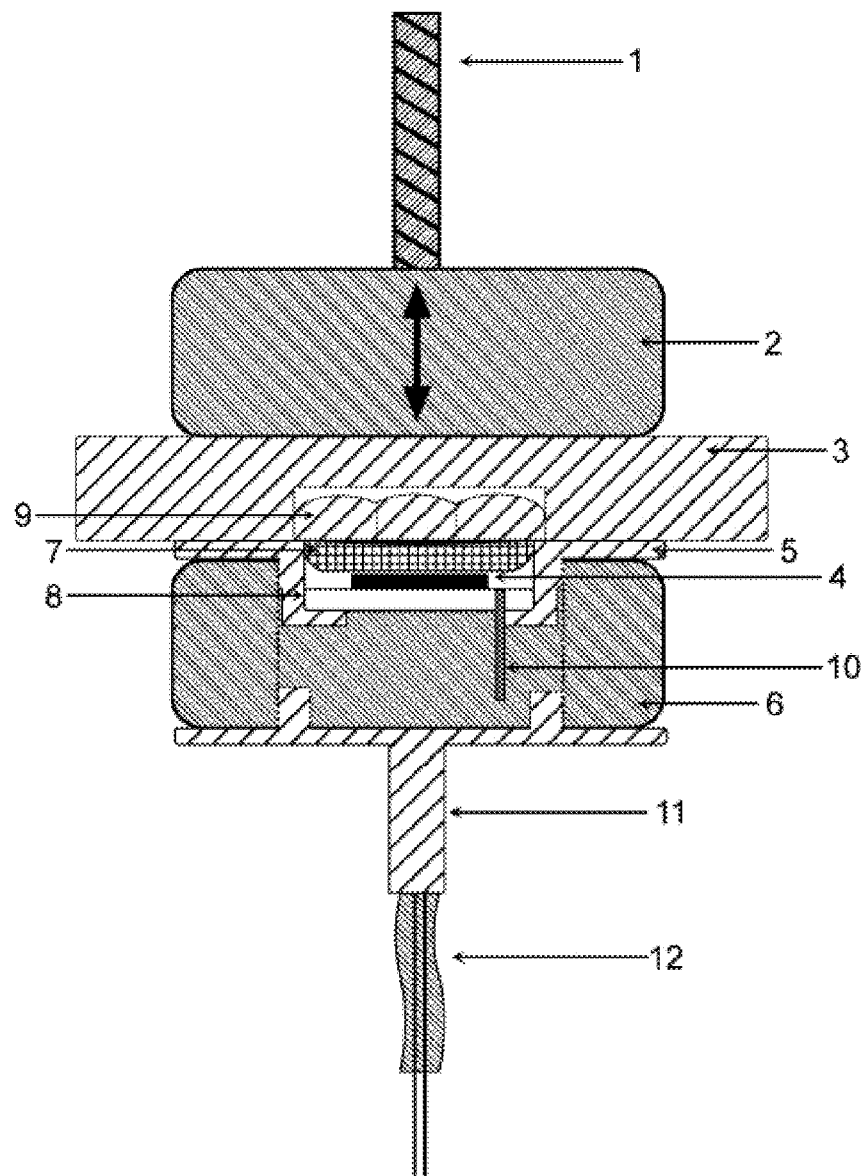
FIG. 2 shows a schematic sectional view of the measurement device of the invention according to another preferred embodiment.

FIG. 2 shows another embodiment of the measurement device of the invention. The basic structure corresponds to that of FIG. 1. However, FIG. 2 shows that the sensor clamp element, and in particular the counter stamp 3, has a structure in the form of a depression. As shown in FIG. 2, needles of a conifer are received in the step. This leads to a good contact with the needles.

Figure 3:
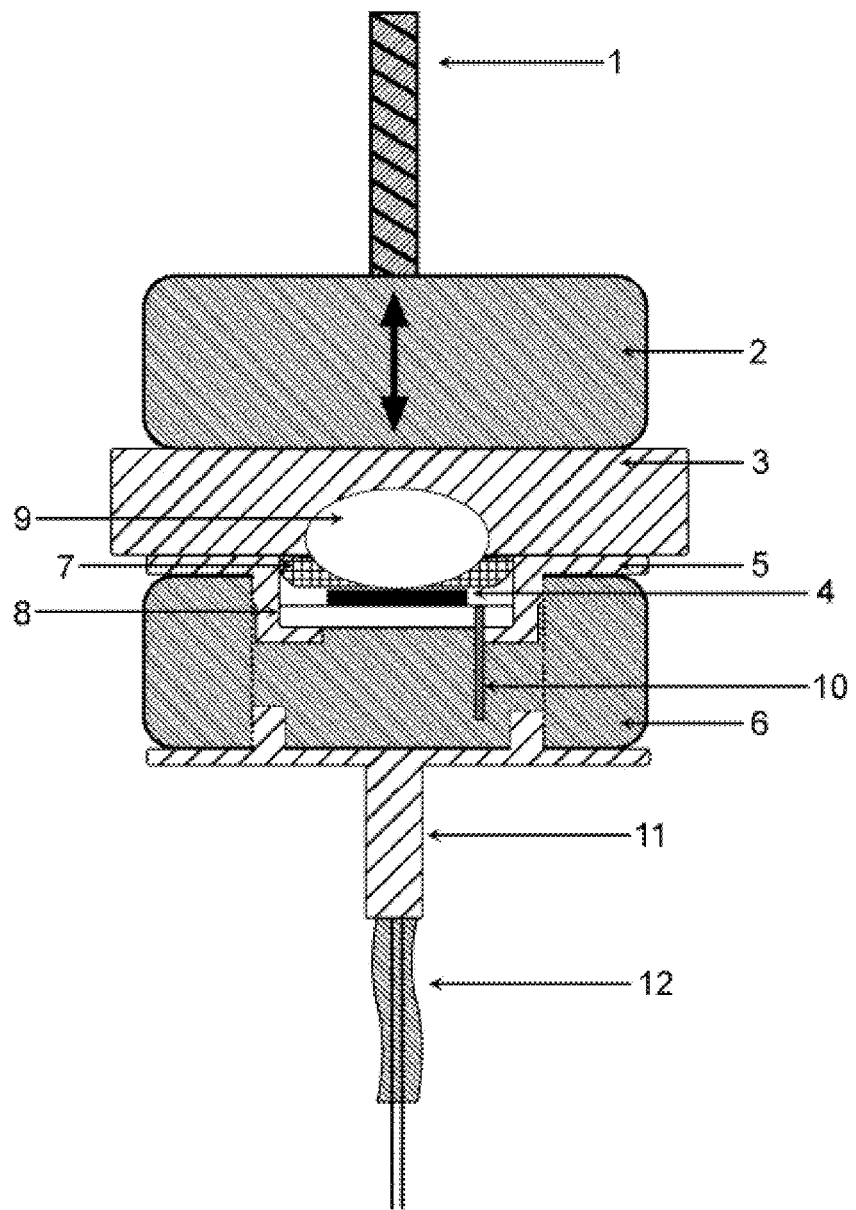
FIG. 3 shows a schematic sectional view of the measurement device of the invention according to another preferred embodiment.

FIG. 3 shows another embodiment of the measurement device of the invention. The basic structure corresponds to that of FIG. 1. However, FIG. 2 shows that the counter clamp element 3 and the sensor clamp element have a depression for receiving, e.g., a fruit stem therein.

Figure 4:
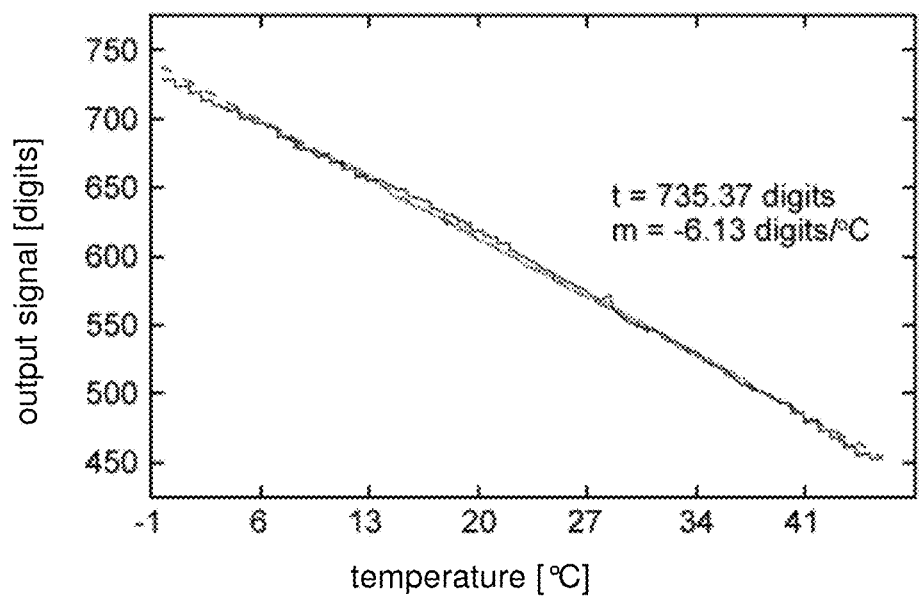
FIG. 4 shows an example of a calibration line for the temperature compensation.

FIG. 4 shows an example of a calibrating line for the temperature compensation for a probe. The output signals of the probes are shown in digits against the temperature in degrees Celsius. Based on this regression line, the gradient (m; in the example: m=−6.13 digits/° C.) as well as the y-axis section (t; in the example: t=735.37 digits) are determined. For compensating for the temperature dependency, $V[p]$ (compensated output signal) is calculated in accordance with the equation $V[p]=V[p, T]-((T \cdot m)+t)$, as discussed. Since, in accordance with the above equation, the probe signal is also dependent on the pressure, subsequently the temperature dependency of the probe is determined in that the probe is calibrated in accordance with the air pressure. By using suitable software, the temperature-compensated signal $V[p]$ is stored in the database and visualized accordingly.

Figure 5:
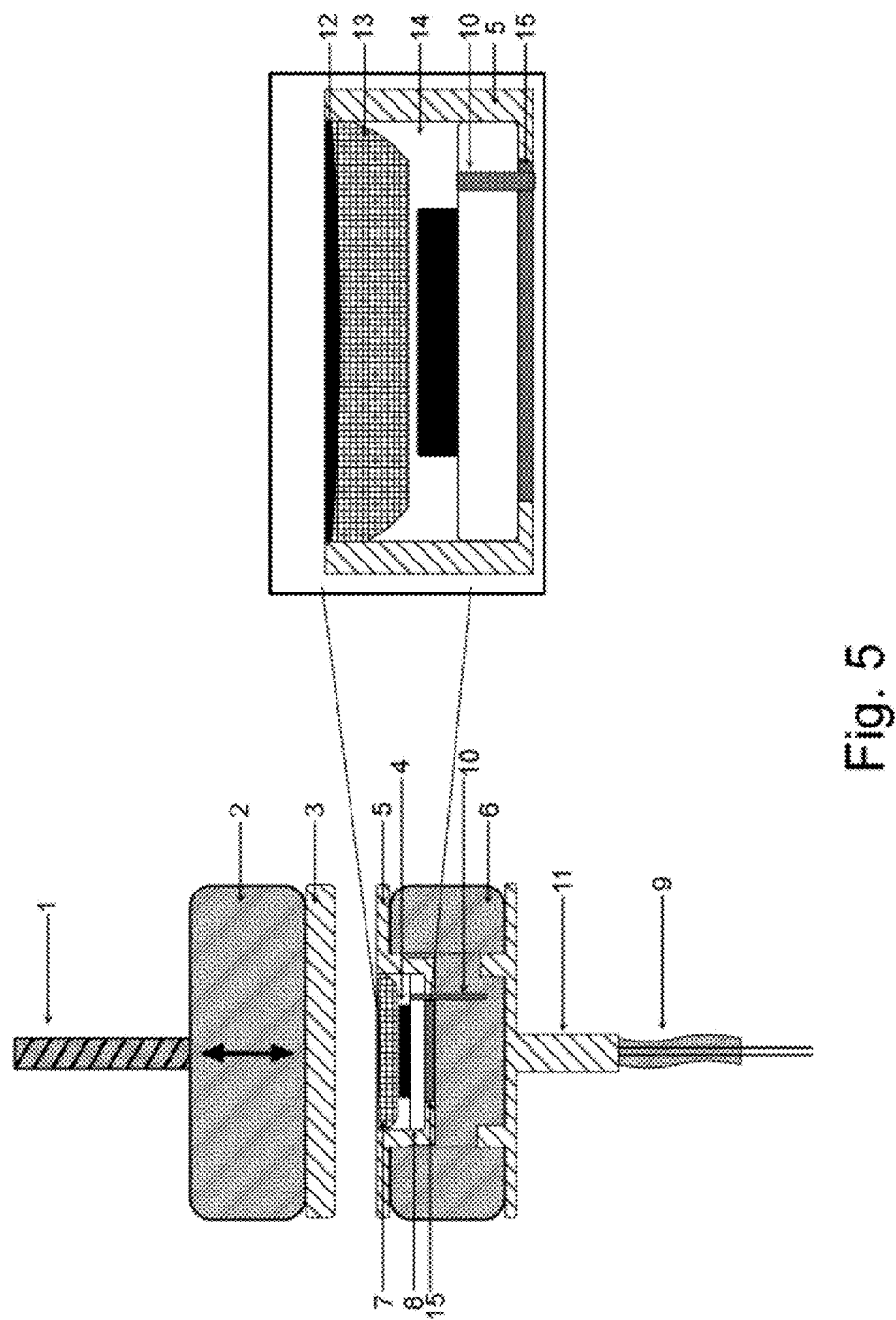
FIG. 5 shows a schematic sectional view of the measurement device of the invention according to a further preferred embodiment.

FIG. 5 shows a further preferred embodiment of the measurement device of the invention. The shown measurement device again comprises a clamp element in the form of a magnet 6. The clamp element 6 in turn has a depression in which a sensor holder 5 is arranged, said sensor holder forming the top of the clamp element facing the plant sample. A sensor insert is received in the depression of the sensor holder. The sensor insert comprises a printed circuit board or lead frame 8 which holds a pressure sensor 4. The pressure sensor 4 is connected with an evaluation device via activation lines 9 or via a wireless connection.

As shown in the enlarged view of FIG. 5, also the pressure sensor of this clamp element of the invention is cast or embedded in the depression of the sensor holder. According to the invention, this is preferably done in three steps or stages, which are shown by the three layers 14, 13 and 12. Polymer layer 14 is the layer which is filled in first and raises at the wall of the sensor insert. The second polymer layer 13 is applied on top thereof, before then the final layer 12 is cast.

In this embodiment, below the printed circuit board/lead frame 8 comprising the pressure sensor 4, a further polymer layer is provided as a stop layer 15 for shielding the pressure sensor 4 together with the printed circuit board 8 against the outer atmosphere (moisture, temperature, etc.). The stop layer is preferably made of a heat conductive material, e.g., a polymer, a membrane, wax, a viscous solution or a water-repellent substance.

For ventilation during casting, also this embodiment comprises a through channel 10. The latter extends through the printed circuit board 8, the stop layer 15 and the magnet 6, to allow air that is present in the recess to escape when potting material is filled in. Alternatively, the through channel does not extend through the stop layer, because it can be considered to be sufficient for ventilation if air that is present during the introduction of the stop layer can escape.

At the lower end, i.e. on the side facing away from the plant sample, preferably an end housing 11 is provided.

FIG. 5 moreover shows the counter clamp element with a counter stamp 3, a magnet 2 and a rod with a screw thread 1.

As shown in FIG. 5, the surface of the clamp element and also the surface of the counter stamp 3 are planar, as already explained above in connection with FIG. 1. As exemplarily shown in FIG. 2, however, also for this embodiment other surfaces are conceivable, for example for measuring other plant parts, e.g. a stem or a needle.

When producing the clamp element, first the stop layer is formed at the bottom of the recess of the magnet 6. Then, first the printed circuit board/lead frame with the pressure sensor arranged thereon is glued to the bottom of the recess of the magnet 6. Then, a first amount of potting material 14 is filled into the recess, wherein the first amount is selected such that only the printed circuit board/lead frame and the pressure sensor are covered and the potting compound can raise at the lower half of the inner wall of the sensor housing. After the first amount of potting material has cross-linked with the printed circuit board/lead frame, the pressure sensor and the inner wall and has cured, a second amount of potting material 13 is filled in so that, taking into account the expansion during cross-linking of the second amount of potting material with the wall of the recess, the second amount of potting material remains below the upper edge of the recess. Finally, after the second amount of potting material has cross-linked with the recess wall, a third amount of potting material 12 is filled in so that the top of the potting material 12 lies flush with the first contact surface of the sensor holder 5.

Figure 6:
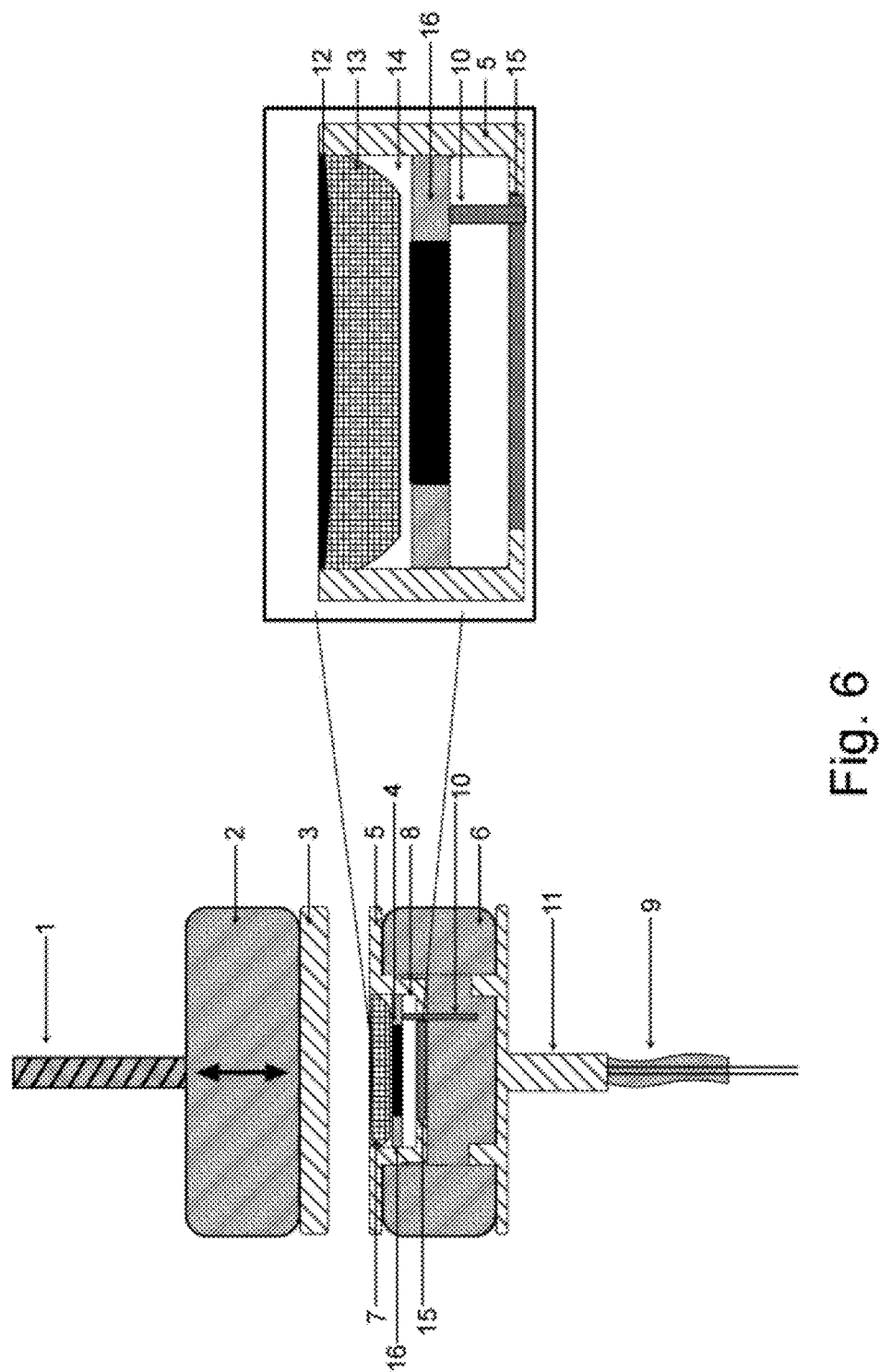
FIG. 6 shows a schematic sectional view of the measurement device of the invention according to a further preferred embodiment.

The embodiment shown in FIG. 6 substantially corresponds to the embodiments described above. In order to avoid repetitions, only the differentiating features are described in the following.

In the embodiment of FIG. 6, the pressure sensor is additionally coated with a curing polymer. The latter is marked with reference number 16 in FIG. 6. Said polymer (e.g., Hysol FP4451TD) is introduced into the recess in the magnet before the space over it is filled with silicone or another polymer in the described three or more steps. The polymer is filled in up to the upper edge of the sensor. This guarantees that corners and edges are always uniformly filled by the silicone or polymer that is then introduced, and the polymerization takes place uniformly and completely in such critical areas.

Figure 7:
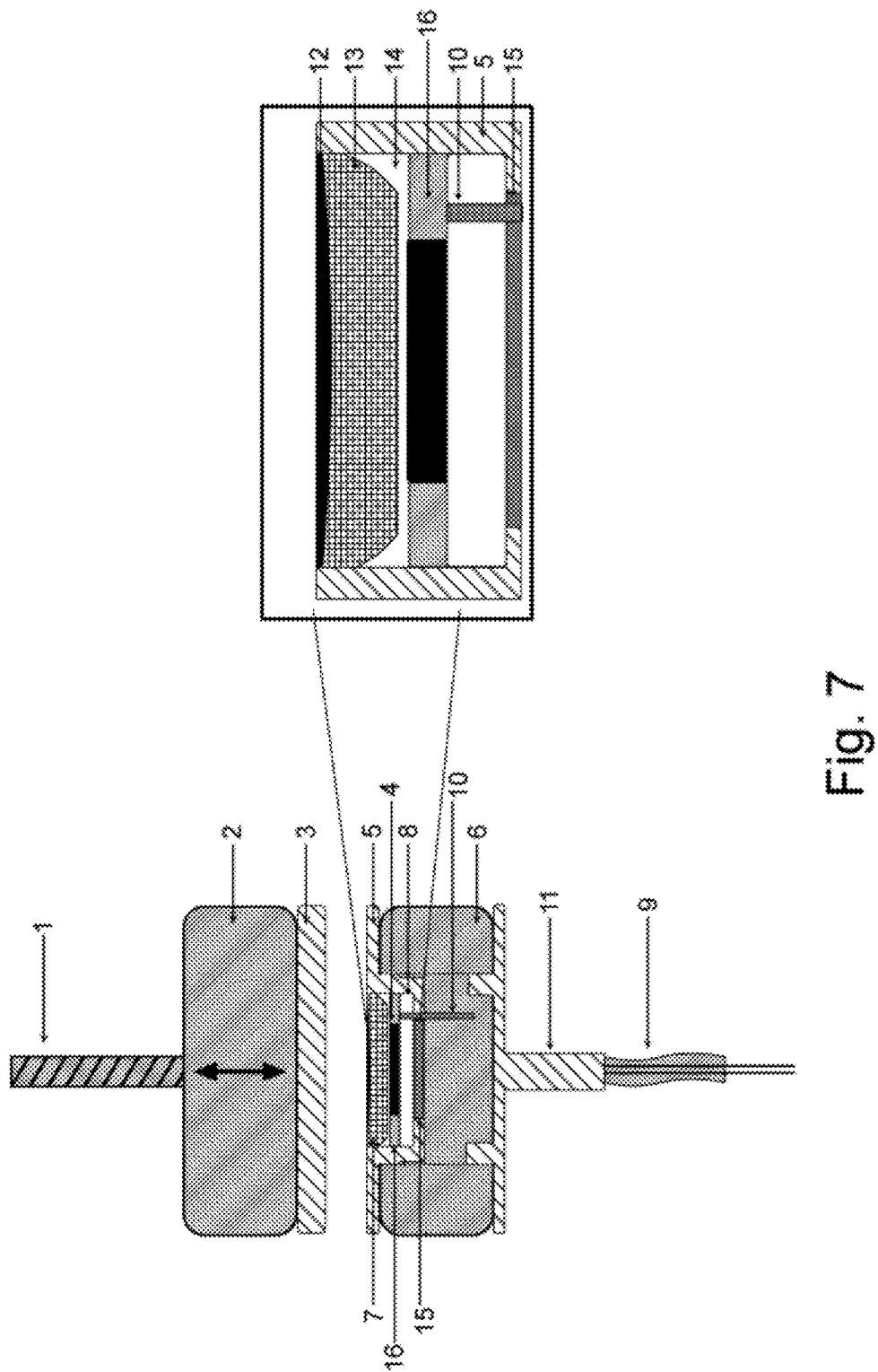
FIG. 7 shows a schematic sectional view of the measurement device of the invention according to a further preferred embodiment.

A further modification of the measurement device is shown in FIG. 7. Here, the inner wall of the sensor holder 5 is cone-shaped, with a diameter that decreases towards the opening. Such a taper can be used for all discussed embodiments of the invention to guarantee a better fixation of the uppermost polymer layer. Tearing-off of the last layer is thus prevented more reliably.

Although the invention is illustrated and described in detail on the basis of the Figures and the corresponding description, this illustration and this detailed description are meant to be illustrative and exemplary and not as limiting the invention. It goes without saying that experts can make changes and modifications without leaving the scope of the following claims. In particular, the invention also comprises embodiments with any combination of features which have been mentioned or shown above in connection with various aspects and/or embodiments.

The invention also comprises individual features in the Figures, even if they are shown therein in connection with other features and/or have not been mentioned above.

Furthermore, the term "comprise" and derivations thereof do not exclude other elements or steps. Moreover, the indefinite articles "a" and "an" and derivations thereof do not exclude a plurality. The functions of several features mentioned in the claims can also be fulfilled by a unity. The terms "substantially", "about", "approximately" and the like in connection with a property or a value, in particular also define exactly this property or exactly this value. All reference numbers in the claims should not be understood as restricting the scope of the claims.

The invention claimed is:

1. A method for producing a clamp element for a turgor pressure measurement device for measuring the turgor pressure in a plant sample, wherein the clamp element comprises:
a sensor receiving portion with a first contact surface, a surface lying opposite the contact surface, and a peripheral surface connecting the two, wherein the clamp element has a longitudinal axis extending perpendicularly to the first contact surface, and with a recess on the side of the first contact surface, said recess being open towards the first contact surface;
a pressure sensor, which is arranged on a printed circuit board/lead frame, to measure a pressure response signal of the plant sample, wherein the printed circuit board/lead frame is arranged with the pressure sensor in the recess of the sensor receiving portion such that the pressure sensor faces the first contact surface and the printed circuit board/lead frame lies at the bottom of the recess, characterized by the steps:
(a) fixing the printed circuit board/lead frame with the pressure sensor arranged thereon at the bottom or at the wall of the recess;
(b) filling a first amount of potting material into the recess, wherein the first amount is selected such that only the printed circuit board/lead frame and the pressure sensor are covered and the potting material can raise at the lower half of the inner wall of the sensor housing;
(c) after cross-linking of the first amount of potting material with the printed circuit board/lead frame, the pressure sensor and the inner wall, filling in a second amount of potting material such that, taking into account the expansion during cross-linking of the second amount of potting material with the wall of the recess, the second amount of potting material remains below the upper edge of the recess; and (d) after cross-linking of the second amount of potting material with the recess wall, filling in a third amount of potting material such that the top of the potting material lies flush with the first contact surface.

2. The method according to claim 1, further comprising the step: before completely curing of the third amount of potting material, forming a negative top structure on the surface of the potting material in accordance with a surface structure of a plant.

3. The method according to claim 2, wherein the negative top structure is stamped into the surface of the potting material.

4. The method according to claim 3, wherein the top structure is formed by means of a counter clamp element of the turgor pressure measurement device having a corresponding counter structure.

5. The method according to claim 2, wherein the negative top structure is substantially concave.

6. The method according to claim 1, further comprising the step: after completely curing of the third amount of potting material, forming a negative top structure on the surface of the potting material in accordance with a surface structure of a plant.

7. The method according to claim 6, wherein the top structure is formed by means of a counter clamp element of the turgor pressure measurement device having a corresponding counter structure.

8. The method according to claim 7, wherein the top structure is formed by stamping by means of the counter clamp element of the turgor pressure measurement device at a temperature of about 30° C. for a time period of 24 to 120 hours.

9. The method according to claim 8, wherein a transfer material is clamped between the third amount of potting material of the clamp element and the counter clamp element, wherein the time period is to be selected depending on the transfer material.

10. A clamp element for a turgor pressure measurement device for measuring the turgor pressure in a plant sample, produced in accordance with the method according to claim 1.

11. A clamp element for a turgor pressure measurement device for measuring the turgor pressure in a plant sample, wherein the clamp element comprises:
a sensor receiving portion with a first contact surface, a surface lying opposite the contact surface, and a peripheral surface connecting the two, wherein the clamp element has a longitudinal axis extending perpendicularly to the first contact surface, and with a recess on the side of the first contact surface, wherein the recess is open towards the first contact surface, and wherein the sensor receiving portion has a through channel extending from the interior of the recess to an outer surface;
a first force element which is arranged on the surface of the sensor receiving portion which is opposite the first contact surface;
a pressure sensor, which is arranged on a printed circuit board/lead frame, to measure a pressure response signal of the plant sample, wherein
the printed circuit board/lead frame with the pressure sensor is arranged in the recess of the sensor receiving portion such that the pressure sensor faces the first contact surface and the printed circuit board/lead frame lies at the bottom of the recess; and wherein the printed circuit board/lead frame has a through channel extending from the side of the printed circuit board/lead frame which faces the recess opening to the side facing the bottom of the recess, wherein the opening of the through channel on the side facing the bottom is flush with the inner opening of the through channel of the sensor receiving portion; and
wherein the recess is filled with a cured potting material with homogeneous top at the first contact surface.

12. The clamp element according to claim 11, wherein the printed circuit board/lead frame comprises at least two through channels extending from the side of the printed circuit board/lead frame facing the recess opening to the side of the printed circuit board/lead frame facing the bottom of the recess.

13. The clamp element according to claim 12, wherein the sensor receiving portion comprises at least two through channels extending from the interior of the recess to an outer surface, wherein the openings of the through channels on the side of the printed circuit board/lead frame facing the bottom of the recess are flush with inner openings of the through channels of the sensor receiving portion.

14. The clamp element according to claim 11, wherein the printed circuit board/lead frame has a thermal expansion coefficient in the x and y directions of less than $12\times10^{-6}$ $K^{-1}$, in particular less than $16\times10^{-6}$ $K^{-1}$.

15. The clamp element according to claim 11, wherein the printed circuit board/lead frame has a thermal expansion coefficient in the z direction of less than $40\times10^{-6}$ $K^{-1}$, in particular less than $60\times10^{-6}$ $K^{-1}$.

16. The clamp element according to claim 11, wherein the pressure sensor is glued to the printed circuit board/lead frame.

17. The clamp element according to claim 11, wherein the potting material comprises a cross-linkable polymer or consists of a cross-linkable polymer.

18. The clamp element according to claim 17, wherein the potting material is selected from epoxy resin, silicone, additively cross-linking silicone, silicone cross-linking in a condensing manner, organic hydrogel or natural hydrogel having a thermal conductivity of $>0.4$ Watt$\times m^{-1} \times K^{-1}$.

19. The clamp element according to claim 18, wherein the material of the adhesive has an expansion coefficient which is similar to that of the potting material.

20. The clamp element according to claim 11, wherein the cross-section of the printed circuit board/lead frame corresponds to the cross-section of the recess.

21. The clamp element according to claim 11, wherein the sensor receiving portion comprises an adhesive layer between the bottom or the wall of the recess and the side of the printed circuit board/lead frame facing the bottom/wall.

22. The clamp element according to claim 11, wherein the walls of the recess of the sensor receiving portion are not provided with an adhesion promoter.

23. A clamp element for a turgor pressure measurement device for measuring the turgor pressure in a plant sample, comprising:
a sensor receiving portion with a first contact surface, a surface lying opposite the contact surface, and a peripheral surface connecting the two, wherein the clamp element has a longitudinal axis extending perpendicularly to the first contact surface, and with a recess on the side of the first contact surface, said recess being open towards the first contact surface,
a pressure sensor, which is arranged on a printed circuit board/lead frame, to measure a pressure response signal of the plant sample, the printed circuit board/lead frame with the pressure sensor being arranged in the recess of the sensor receiving portion such that the pressure sensor faces the first contact surface and the printed circuit board/lead frame lies at the bottom of the recess; and
wherein the recess is filled with a cured potting material which is not transparent to ultraviolet radiation.

24. The clamp element according to claim 23, wherein the potting material comprises a dye which is not transparent to ultraviolet radiation.

25. A clamp element for a turgor pressure measurement device for measuring the turgor pressure in a plant sample, wherein the clamp element comprises:
a sensor receiving portion with a first contact surface, a surface lying opposite the contact surface, and a peripheral surface connecting the two, wherein the clamp element has a longitudinal axis extending perpendicularly to the first contact surface, and with a recess on the side of the first contact surface, wherein the recess is open towards the first contact surface;
a force element which is arranged on the surface of the sensor receiving portion which is opposite the first contact surface;
a pressure sensor, which is arranged on a printed circuit board/lead frame, to measure a pressure response signal of the plant sample, the printed circuit board/lead frame with the pressure sensor being arranged in the recess of the pressure receiving portion such that the pressure sensor faces the first contact surface and the printed circuit board/lead frame lies at the bottom of the recess;
wherein the recess is filled with a cured potting material with homogeneous top at the first contact surface; and
wherein the clamp element is temperature-compensated as a whole.

26. The clamp element according to claim 25, wherein the clamp element is temperature-compensated as a whole by linear regression.

27. The clamp element according to claim 25, wherein the sensor receiving portion comprises a through channel extending from the interior of the recess to an outer surface, and wherein the printed circuit board/lead frame comprises a through channel extending from the side of the printed circuit board/lead frame facing the recess opening to the side facing the bottom of the recess, wherein the opening of the through channel on the side facing the bottom is flush with the inner opening of the through channel of the sensor receiving portion.

28. A turgor pressure measurement device for measuring the turgor pressure in a plant sample, comprising:
(a) a first clamp element comprising:
a sensor receiving portion with a first contact surface, a surface lying opposite the contact surface, and a peripheral surface connecting the two, wherein the clamp element has a longitudinal axis extending perpendicularly to the first contact surface, and with a recess on the side of the first contact surface, wherein the recess is open towards the first contact surface;
a first force element which is arranged on the surface of the sensor receiving portion opposite the first contact surface;
a pressure sensor, which is arranged on the printed circuit board/lead frame, to measure a pressure response signal of the plant sample, the printed circuit board/lead frame with the pressure sensor being arranged in the recess of the sensor receiving portion such that the pressure sensor faces the first contact surface and the printed circuit board/lead frame lies at the bottom of the recess;
wherein the recess is filled with a cured potting material with homogeneous top at the first contact surface;

(b) a second clamp element comprising:
a counter clamp part with a second contact surface, a surface lying opposite the second contact surface, and a peripheral surface connecting the two;
a second force element arranged on the side opposite the second contact surface;
wherein one of the two force elements has a magnet; and
wherein the turgor pressure measurement device is temperature-compensated as a whole.

29. The turgor pressure measurement device according to claim 28, wherein the clamp element is temperature-compensated as a whole by linear regression.

30. The turgor pressure measurement device according to claim 29, wherein the sensor receiving portion comprises a through channel extending from the interior of the recess to an outer surface, and wherein the printed circuit board/lead frame comprises a through channel extending from the side of the printed circuit board/lead frame facing the recess opening to the side facing the bottom of the recess, wherein the opening of the through channel on the side facing the bottom is flush with the inner opening of the through channel of the sensor receiving portion.

31. The turgor pressure measurement device according to claim 30, wherein the printed circuit board/lead frame comprises at least two through channels extending from the side of the printed circuit board/lead frame facing the recess opening to the side of the printed circuit board/lead frame facing the bottom of the recess.

32. The turgor pressure measurement device according to claim 31, wherein the sensor receiving portion comprises at least two through channels extending from the interior of the recess to an outer surface, wherein the openings of the through channels on the side of the printed circuit board/lead frame facing the bottom of the recess are flush with inner openings of the through channels of the sensor receiving portion.

33. The turgor pressure measurement device according to claim 29, wherein the printed circuit board/lead frame has a thermal expansion coefficient in the x and y directions of less than $12 \times 10^{-6}$ K$^{-1}$, in particular less than $16 \times 10^{-6}$ K$^{-1}$.

34. The turgor pressure measurement device according to claim 29, wherein the printed circuit board/lead frame has a thermal expansion coefficient in the z direction of less than $40 \times 10^{-6}$ K$^{-1}$, in particular less than $60 \times 10^{-6}$ K$^{-1}$.

35. The turgor pressure measurement device according to claim 29, wherein the pressure sensor is glued to the printed circuit board/lead frame.

36. The turgor pressure measurement device according to claim 29, wherein the potting material comprises a cross-linkable polymer or consists of a cross-linkable polymer.

37. The turgor pressure measurement device according to claim 36, wherein the potting material is selected from epoxy resin, silicone, additively cross-linking silicone, silicone cross-linking in a condensing manner, organic hydrogel or natural hydrogel having a thermal conductivity of >0.4 Watt× m$^{-1}$×K$^{-1}$.

38. The turgor pressure measurement device according to claim 29, wherein the cross-section of the printed circuit board/lead frame corresponds to the cross-section of the recess.

39. The turgor pressure measurement device according to claim 29, wherein the sensor receiving portion comprises an adhesive layer between the bottom or the wall of the recess and the side of the printed circuit board/lead frame facing the bottom/wall.

40. The turgor pressure measurement device according to claim 39, wherein the material of the adhesive has an expansion coefficient which is similar to that of the potting material.

41. The turgor pressure measurement device according to claim 29, wherein the potting material is not transparent to ultraviolet radiation.

42. The turgor pressure measurement device according to claim 41, wherein the potting material comprises a dye which is not transparent to ultraviolet radiation.

43. The turgor pressure measurement device according to claim 42, wherein the dye was degassed for one day at a negative pressure of at least 700 kPa before being mixed with the potting material.

44. The turgor pressure measurement device according to claim 29, wherein the walls of the recess of the sensor receiving portion are not provided with an adhesion promoter.

45. The turgor pressure measurement device according to claim 29, wherein the second contact surface of the second clamp element is structured.

46. The turgor pressure measurement device according to claim 45, wherein the structure is in the form of a relief.

47. The turgor pressure measurement device according to claim 46, wherein the structure is in the form of concentric rings.

48. The turgor pressure measurement device according to claim 46, wherein the structure is in the form of parallel grooves, with the groove being closest to the longitudinal axis being deeper than the remaining grooves.

49. A method for the temperature compensation for a clamp element of a turgor pressure measurement device for measuring the turgor pressure in a plant sample, wherein the clamp element or its measurement signal is subjected as a whole to temperature compensation by linear regression.

50. The method according to claim 49, comprising the steps:
  (a) determining a regression line for the temperature dependency of the output signal of the measurement device; and
  (b) calculating a compensated pressure signal in accordance with the equation $$V[p]=V[p,T]-((T \cdot m)+t),$$

wherein:
  V[p, T] is the output signal which depends on pressure and temperature,
  T is the temperature;
  m is the gradient of the regression line; and
  t is the y-axis section of the regression line.

51. The method according to claim 50, wherein step (a) comprises the steps:
  (a1) applying a gradual temperature increase to the measurement device in stages of 10° C. from 0° C. to 50° C. in intervals of at least 30 min each;
  (a2) measuring the output signal of the measurement device at the respective stage; and
  (a3) determining the regression line based on the measurement values.

52. The method according to claim 50, further comprising the steps:
  (c) calibrating the probe in accordance with the air pressure; and
  (d) storing the temperature-compensated signal V[p] for each measurement device in a database.

53. The method according to claim 49, comprising the steps:
  (a) determining a regression line for the temperature dependency of the output signal of the measurement device;
  (b) connecting an electrical component in series with the output signal of the pressure sensor chip of the measurement device, wherein the electrical component has a temperature dependency being contrary to the regression line.

54. The method for the temperature compensation for a turgor pressure measurement device for measuring the turgor pressure in a plant sample, wherein the measurement device or its measurement signal is subjected as a whole to temperature compensation by linear regression.

55. A method for operating a turgor pressure measurement device for measuring the turgor pressure of a plant sample, comprising:
  (a) a first clamp element which comprises:
    a sensor receiving portion with a first contact surface, a surface lying opposite the contact surface, and a peripheral surface connecting the two, wherein the clamp element has a longitudinal axis extending perpendicularly to the first contact surface, and with a recess on the side of the first contact surface, wherein the recess is open towards the first contact surface;
    a first force element which is arranged on the surface of the sensor receiving portion which is opposite the first contact surface;
    a pressure sensor, which is arranged on a printed circuit board/lead frame, to measure a pressure response signal of the plant sample, the printed circuit board/lead frame being arranged with the pressure sensor in the recess of the sensor receiving portion such that the pressure sensor faces the first contact surface and the printed circuit board/lead frame lies at the bottom of the recess;
    wherein the recess is filled with a cured potting material with a homogeneous top at the first contact surface;
  (b) a second clamp element which comprises:
    a counter clamp part with a second contact surface, a surface lying opposite the second contact surface, and a peripheral surface connecting the two;
    a second force element which is arranged on the side opposite the second contact surface;
  wherein the method comprises the steps:
  alternately measuring a pressure response signal of the plant sample in a pressure measurement mode of the measurement device and measuring the temperature of the surface of the plant sample in a temperature mode of the measurement device.

56. The method according to claim 55, wherein the pressure measurement sensor is operated alternately in a pressure measurement mode and a temperature measurement mode.

57. The method according to claim 56, wherein it is shifted continuously between the pressure measurement mode and the temperature measurement mode.

58. The method according to claim 57, wherein it is shifted in intervals of 1 to 2 MS.

59. A method for operating a system consisting of a plurality of turgor pressure measurement devices for measuring the turgor pressure in a plant sample, which are attached to the same plant sample and have distance sensors for determining the distances between the measurement devices, comprising the steps:
  detecting the distances between the measurement devices in pairs with respect to each other at two subsequent time points, and comparing the detected distance values for each individual pair of measurement devices to determine the plant growth.

60. A method for operating a system consisting of a plurality of turgor pressure measurement devices for measuring the turgor pressure in a plant sample, which are attached to the same plant, and wherein a measurement device and/or a separate device comprises an electromagnet that can be activated, comprising the steps:
applying a pressure pulse to the plant sample by means of the electromagnet;
detecting the pressure pulse propagating in the plant sample at the measurement devices;
determining the propagating speed of the pressure pulse based on the time distance between pressure pulse generation and detection at the measurement devices for each measurement device and on the local distance between the measurement device/device generating the pressure pulse and the detecting measurement device; and
determining the proportion of water-filled and air-filled spaces in the tissue of the plant sample based on the propagation speed of the pressure pulse.

61. A system for plant watering comprising a plurality of turgor pressure measurement devices for measuring the turgor pressure in a plant sample and a measurement device for detecting the activity of social pollinators, wherein in case an activity of the social pollinators is detected and at the same time a water shortage in the plant is detected, watering is activated.

62. The clamp element according to claim, wherein the potting material is not transparent to ultraviolet radiation.

63. The clamp element according to claim 62, wherein the potting material comprises a dye which is not transparent to ultraviolet radiation.

64. The clamp element according to claim 63, wherein the dye was degassed for one day at a negative pressure of at least 700 kPa before being mixed with the potting material.

* * * * *